US00PP10617P

United States Patent [19]

Austin

[11] Patent Number: Plant 10,617

[45] Date of Patent: Sep. 29, 1998

[54] SHRUB ROSE PLANT NAMED 'AUSKY'

[75] Inventor: David Charles Henshaw Austin, Albrighton, England

[73] Assignee: David Austin Roses Limited, Albrighton, England

[21] Appl. No.: 788,677

[22] Filed: Jan. 24, 1997

[51] Int. Cl.[6] ..... A01H 5/00

[52] U.S. Cl. ..... Plt./1

[58] Field of Search ..... Plt./1, 7.1, 22, Plt./9, 26

*Primary Examiner*—Howard J. Locker

*Attorney, Agent, or Firm*—Klarquist Sparkman Campbell Leigh & Whinston, LLP

[57] ABSTRACT

A shrub rose plant having no observed disease susceptibility; excellent repeat flowering; attractive; strong pink, small flowers held in large bunches; and attractive shrubby growth.

1 Drawing Sheet

The present invention relates to a new and distinct variety of shrub rose plant of the *Rosa hybrida* class which was originated by me by crossing two existing varieties, Martin Frobisher, unpatented, and Blush Noisette, unpatented.

The primary objective of this breeding was to produce a new shrub rose variety having the extreme disease resistance of Martin Frobisher with the very excellent repeat flowering qualities of Blush Noisette. The objective was substantially achieved, along with other desirable improvements, as evidenced by the following unique combination of characteristics that are outstanding in the new variety and that distinguish it from its parents, as well as from all other varieties of which I am aware:

1. No observed disease susceptibility;
2. Excellent repeat flowering;
3. Attractive strong pink, small flowers held in large bunches;
4. Attractive shrubby growth.

Asexual reproduction of this new variety by budding, as performed at Albrighton, Wolverhampton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Martin Frobisher.

*Pollen parent.*—Blush Noisette.

Classification:

*Botanical.*—*Rosa hybrida.*

*Commercial.*—Shrub.

FLOWER

Observations made from specimens grown in a garden environment at Albrighton, Wolverhampton, England in July 1993.

Blooming habit: Recurrent.

Bud:

*Size.*—0.75 inches long when the petals start to unfurl.

*Form.*—The bud form is short, pointed ovoid, fairly broad based.

*Color.*—When sepals first divide, bud color is Red Group 53C/D. When half blown, the upper sides of the petals are Red-Purple Group 61B/C/D; and the lower sides of the petals are Red-Purple Group 58C/D.

*Sepals.*—Color: Yellow-Green Group 144A/B with overlying blush of Greyed-Red Group 182A. Surface texture: Smooth, slightly leathery. There are five unappendaged sepals with slightly hairy edges.

*Receptacle.*—Color: Yellow-Green Group 144A with an overlying blush of Greyed-Red Group 182A. Shape: Goblet. Size: Small, 0.25 inches×0.20 inches. Surface: Smooth.

*Peduncle.*—Length: Variable, medium, averaging about 1.5 inches. Surface: Smooth. Color: Light green; bronzy. Strength: Erect; slender.

Bloom:

*Size.*—Small. Average open size is 2 inches.

*Borne.*—Several together and in clusters of up to 25 small flowers. If in clusters: Irregular shape.

*Stems.*—Medium, short, normal strength.

*Form.*—When first open: High centered. Permanence: Outer petals curl back, all petals curl.

*Petalage.*—Number of petals under normal conditions: 90–100.

*Color.*—The upper sides of the petals overall give the appearance of Red-Purple Group 62B/C, the inner petals being darker (Red-Purple Group 58C) than the outer petals (Red-Purple Group 62C/D). The reverse sides of the petals are Red-Purple Group 65B. The base of each petal is white with pale, Yellow Group 4D midline. The major color on the upper sides is Red-Purple Group 62B.

*Variegations.*—None.

*Discolorations.*—The general tonality at the end of the first day: Pale to Red-Purple Group 69A and Red-Purple Group 65B. At the end of the third day: Red-Purple Group 69B.

*Fragrance.*—Very slight.

Petals:

*Textures.*—Thin.

*Shape.*—Inner are oval; outer are notched, deltoid, heart shaped.

*Arrangement.*—Informal, with a few, small petaloids in the center.

*Persistence.*—Petals drop off fairly cleanly before drying.

*Lastingness.*—On the plant: Fair, about 3 to 5 days. As a cut flower: Not tested.

Reproductive parts:

*Anthers.*—Size: Medium. Quantity: Many. Color: Yellow. Arrangement: Tucked in calyx or partly so, mixed with petaloids.

*Filaments.*—Color: White.

*Pollen.*—Color: Pale gold yellow.

*Styles.*—Color: Pale green.

*Stigmas.*—Color: Greenish white.

Form: Bush, shrub.

Growth: Vigorous, upright, branching, fairly compact. Mature plant is about one foot in height and 2.5 feet in width.

Foliage:

*Number of leaflets on normal mid-stem leaves.*—7.

*Size.*—5 to 6 inches long×3.5 to 4.0 inches wide.

*Quantity.*—Abundant, normal.

*Color.*—New foliage: Upper side: Group 146B. Lower side: Yellow-Green 146C. Old foliage: Yellow-Green Group 146A. Lower side: Yellow-Green 146B.

Leaflets:

*Shape.*—Pointed oval, elliptic.

*Texture.*—Upper side: Leathery, fairly smooth.

*Edge.*—Serrated.

*Serration.*—Single, small.

*Petiole, rachis.*—Color: Reddish.

*Petiole underside.*—Rough, with prickles, 1–2 per internode.

*Stipules.*—Medium, serrated, about 0.8 inch long.

*Disease resistance.*—No observed susceptibility to mildew and blackspot under normal growing conditions at Albrighton, Wolverhampton, England.

Wood:

*New wood.*—Color: Reddish Greyed Purple Group 183A. Bark: Smooth.

*Old wood.*—Color: Green (Yellow-Green Group 146A). Bark: Fairly smooth.

Prickles:

*Quantity.*—On lower part of main canes from base: Ordinary, few. On laterals from main canes: Few.

*Form.*—Medium to short, straight or very slightly hooked downward.

*Color when Young.*—Green at the point and red at the base.

*Position.*—On lower nodes.

Small Prickles:

*Quantity.*—On main stalks: Very few. On laterals: Very few.

*Color.*—Grey-Brown Group 199C.

I claim:

1. A new and distinct variety of shrub rose plant of the *Rosa hybrida* class, substantially as herein shown and described, characterized particularly as to novelty by the unique combination of its extreme disease resistance; excellent repeat flowering; attractive strong pink, small flowers held in large bunches; and attractive shrubby growth.

* * * * *

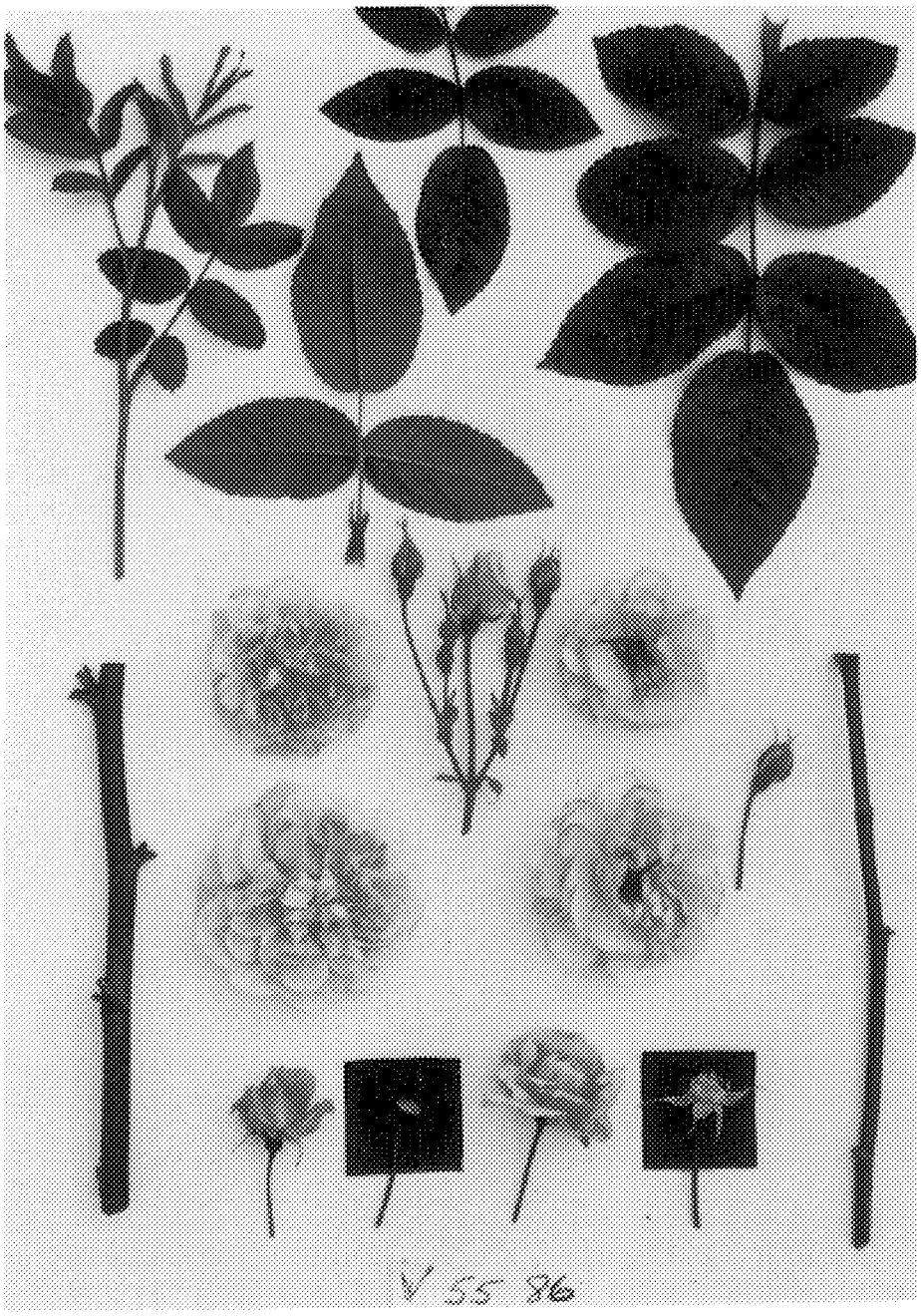
V 55 86

UNITED STATES PATENT AND TRADEMARK OFFICE

CERTIFICATE OF CORRECTION

PATENT NO. : PP. 10,617

DATED : September 29, 1998

INVENTOR(S) : David Charles, et. al.

It is certified that error appears in the above-indentified patent and that said Letters Patent is hereby corrected as shown below:

Column 3, line 19, change "Group 146B." to --Yellow-Green Group 146B.--

Column 3, line 20, after "Old foliage: " insert --Upper side: --.

Column 4, line 6, after "Reddish enclose "Greyed Purple Group 183A" in parentheses, and add a dash between "Greyed" and "Purple"

Signed and Sealed this

Nineteenth Day of October, 1999

*Attest:*

*Attesting Officer*

Q. TODD DICKINSON

*Acting Commissioner of Patents and Trademarks*